United States Patent
Hiniduma-Lokuge et al.

(10) Patent No.: US 8,870,848 B2
(45) Date of Patent: Oct. 28, 2014

(54) SYSTEM AND METHOD FOR DELIVERY OF BIOLOGIC AGENTS

(75) Inventors: Prasanga D Hiniduma-Lokuge, Minneapolis, MN (US); Daniel Sigg, St. Paul, MN (US); Xiaohong Qiu, Rosemount, MN (US)

(73) Assignee: Medtronic, Inc., Minneapolis, MN (US)

( * ) Notice: Subject to any disclaimer, the term of this patent is extended or adjusted under 35 U.S.C. 154(b) by 598 days.

(21) Appl. No.: 12/262,798

(22) Filed: Oct. 31, 2008

(65) Prior Publication Data
US 2010/0114059 A1 May 6, 2010

(51) Int. Cl.
| | | |
|---|---|---|
| A61M 5/24 | (2006.01) | |
| A61M 5/28 | (2006.01) | |
| A61M 5/315 | (2006.01) | |
| A61M 5/00 | (2006.01) | |
| A61M 31/00 | (2006.01) | |
| A61M 37/00 | (2006.01) | |
| A61M 25/00 | (2006.01) | |
| A61M 5/145 | (2006.01) | |

(52) U.S. Cl.
CPC ......... *A61M 37/0069* (2013.01); *A61M 5/2425* (2013.01); *A61M 5/1452* (2013.01); *A61M 5/14566* (2013.01); *A61M 5/2466* (2013.01)
USPC ........ 604/523; 604/93.01; 604/200; 604/218; 604/232

(58) Field of Classification Search
USPC .............. 604/218, 221, 231, 232, 93.01, 523, 604/200–206
See application file for complete search history.

(56) References Cited

U.S. PATENT DOCUMENTS

| | | | | |
|---|---|---|---|---|
| 4,331,146 | A | * | 5/1982 | Brignola .................. 604/200 |
| 5,374,249 | A | * | 12/1994 | Haber et al. .............. 604/91 |
| 5,503,627 | A | | 4/1996 | McKinnon et al. |
| 5,506,125 | A | | 4/1996 | McCabe |
| 5,639,473 | A | | 6/1997 | Grinstaff |
| 5,947,928 | A | | 9/1999 | Muller |
| 5,957,897 | A | * | 9/1999 | Jeffrey .................... 604/223 |
| 5,980,491 | A | * | 11/1999 | Hansen .................... 604/157 |

(Continued)

FOREIGN PATENT DOCUMENTS

WO  WO 99/44656  9/1999

OTHER PUBLICATIONS (PCT/US2009/062552) PCT Notification of Transmittal of the International Search Report and the Written Opinion of the International Searching Authority.

*Primary Examiner* — Emily Schmidt
*Assistant Examiner* — Lauren M Peng
(74) *Attorney, Agent, or Firm* — Carol F. Barry

(57) ABSTRACT

A delivery system for delivering a therapeutic agent to a patient includes a catheter, a stop feature, a container and a bar. The catheter has a proximal end and a distal end and includes a body defining a lumen that extends to the distal end of the catheter. The stop feature is in proximity to the distal end of the catheter. The container is configured to house the therapeutic agent and is insertable and slidably disposable in the lumen of the catheter. The container is also configured to engage the stop feature of the catheter. The bar is slidably disposable in the lumen of the catheter. Sliding of the bar distally in the lumen forces the therapeutic agent out of the container and out of the lumen when the container is engaged with the stop feature. The stop feature is configured to inhibit the container from exiting the lumen.

27 Claims, 18 Drawing Sheets

(56) References Cited

U.S. PATENT DOCUMENTS

| | | |
|---|---|---|
| 6,004,295 A | 12/1999 | Langer et al. |
| 6,221,056 B1 * | 4/2001 | Silverman ............... 604/239 |
| 7,103,418 B2 | 9/2006 | Laske |
| 7,226,441 B2 * | 6/2007 | Kulessa ................ 604/523 |
| 7,252,212 B2 | 8/2007 | Anjanappa et al. |
| 2004/0054327 A1 * | 3/2004 | Gillespie, III ............ 604/135 |
| 2005/0171506 A1 * | 8/2005 | Hallahan et al. ........... 604/514 |
| 2005/0245881 A1 * | 11/2005 | Meyer et al. ............. 604/232 |
| 2006/0111667 A1 * | 5/2006 | Matsuura et al. .......... 604/93.01 |
| 2007/0219507 A1 * | 9/2007 | Dai et al. ............... 604/218 |

* cited by examiner

SYSTEM AND METHOD FOR DELIVERY OF BIOLOGIC AGENTS

FIELD

This disclosure relates to medical devices, systems and methods for delivering biologic agents to a patient.

BACKGROUND

Systems for delivering biologic agents in an operating room setting currently include the biologic agent and a delivery device. A mapping/navigation system, and a monitor for viewing the delivery process may also be used. The biologic agent is typically delivered to the operating room in an appropriate volume and concentration in a closed container, such as an Eppendorf tube. Once in the operating room and when the delivery device is ready to receive this biologic agent, the biologic agent is transferred from the container to a syringe which is in turn connected to the delivery device. The biologic agent is then carefully delivered from the syringe through the delivery device into target tissue.

The steps involved in such a process present several areas for improvement. For example, the transfer of the biologic agent from the container to the delivery system involves exposing the agent to the environment, risking contamination. Also, the transfer provides the potential for spilling and loss of the biologic agent, as well as potentially inaccurate amounts being delivered. Further, the number of different materials that the biologic agent contacts may be quite high. For example, the biologic agent contacts the container, such as the Eppendorf tube, the syringe, and the delivery device, allowing for possible compatibility issues and losses due to adhesion and adsorption to the container, syringe and delivery device.

Another source of potential concern with current methods for delivering biologic agents is excessive shear stress being placed on the biologic agent as it is delivered through the delivery system. The delivery system typically includes catheters having very small inner diameters; e.g., 29-27 G or about 0.007 inches to 0.009 inches. The inner diameters of the catheters are purposefully kept small to reduce dead space and thus to minimize the amount of deliverable biologic agent lost during the procedure. Exposure to shear stress may greatly reduce the efficacy of the biologic agent delivered, particularly cells.

BRIEF SUMMARY

This disclosure describes, inter alia, a system for delivering biologic agents that allows for delivery of biologic agents in a container via a catheter to a target tissue of a patient. As disclosed herein, an appropriate or predetermined amount of biologic agent may be transferred into the container in a sterile environment. In the operating room, the container is placed in a catheter having a distal end implanted at a target tissue site of a patient and is moved to the distal end of the catheter, where its contents are released into the target tissue.

In an embodiment, a delivery system for delivering a therapeutic agent to a patient is described. The delivery system includes a catheter, a stop feature, a container and a bar. The catheter has a proximal end and a distal end and includes a body defining a lumen that extends to the distal end of the catheter. The stop feature is in proximity to the distal end of the catheter. The container is configured to house the therapeutic agent and is insertable and slidably disposable in the lumen of the catheter. The container is also configured to engage the stop feature of the catheter. The bar is slidably disposable in the lumen of the catheter. Sliding of the bar distally in the lumen forces the therapeutic agent out of the container and out of the lumen when the container is engaged with the stop feature. The stop feature is configured to inhibit the container from exiting the lumen.

In an embodiment, a method for delivering a therapeutic agent to a target tissue of a patient is described. The method includes (i) placing a distal end of a catheter having a lumen in the target tissue; (ii) inserting a container housing the therapeutic agent in the lumen proximal to the distal end of the catheter; (iii) moving the container in the lumen distally; and (iv) releasing the therapeutic agent from the container in proximity to the distal end of the catheter.

In an embodiment, a container for housing a therapeutic agent is described. The container includes a body member, a sealing element, and a rupturable membrane. The body member has a proximal end and a distal end and a lumen that extends from the proximal end to the distal end. The sealing element is slidably disposable in the lumen. The sealing element is configured to sealingly engage the body member as the element is slid within the lumen. The rupturable membrane is disposed across the lumen in proximity to the distal end of the body member.

In an embodiment, a delivery system for delivering a therapeutic agent to a patient is described. The delivery system includes a catheter and a container for housing the therapeutic agent. The catheter has a proximal end and a distal end. The catheter has a body that defines a lumen extends from the proximal end to the distal end. The catheter further includes a stop feature in proximity to the distal end. The container is insertable and slidably disposable in the lumen of the catheter. The container is configured to engage the stop feature of the catheter. The system further includes means for forcing therapeutic agent out of the container and out of the lumen when the container engages the stop feature.

One or more of the various embodiments presented herein provide one or more advantages over prior proposed methods, devices or systems for delivering biologic agents to a target tissue of a patient. For example, placing a container housing the biologic agent directly into the delivery system reduces exposure of the biologic agent to the environment and thus reduces the potential for contamination. This also reduces compatibility issues as the number of different materials that the biologic agent is exposed to is reduced, as the biologic agent is present in the container until it is delivered to the patient. Further, the amount of shear stress to which the biologic agent is subject may be greatly reduced, due e.g. to the biologic agent being static with respect to the container for the length of the catheter. These and other advantages will be readily understood from the following detailed description when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

As used herein, the terms "treat", "therapy", and the like mean alleviating, slowing the progression, preventing, attenuating, or curing the treated disease.

As used herein, "disease", "disorder", "condition" and the like, as they relate to a subject's health, are used interchangeably and have meanings ascribed to each and all of such terms.

The present disclosure describes, inter alia, systems, devices and methods for delivering biologic agents to a target tissue of a patient. A container housing a therapeutic agent may be placed directly into a delivery system and delivered to the target tissue site where the therapeutic agent may be released. The therapeutic agent may be a biologic agent, such as a cell, a virus, a polypeptide, a polynucleotide or the like. Many of such biologic agents are susceptible to complications due to shear stress due to their large size or molecular weight. The therapeutic agent may be formulated in a solution, suspension, dispersion, or the like or may be in solid form.

Figure 1:
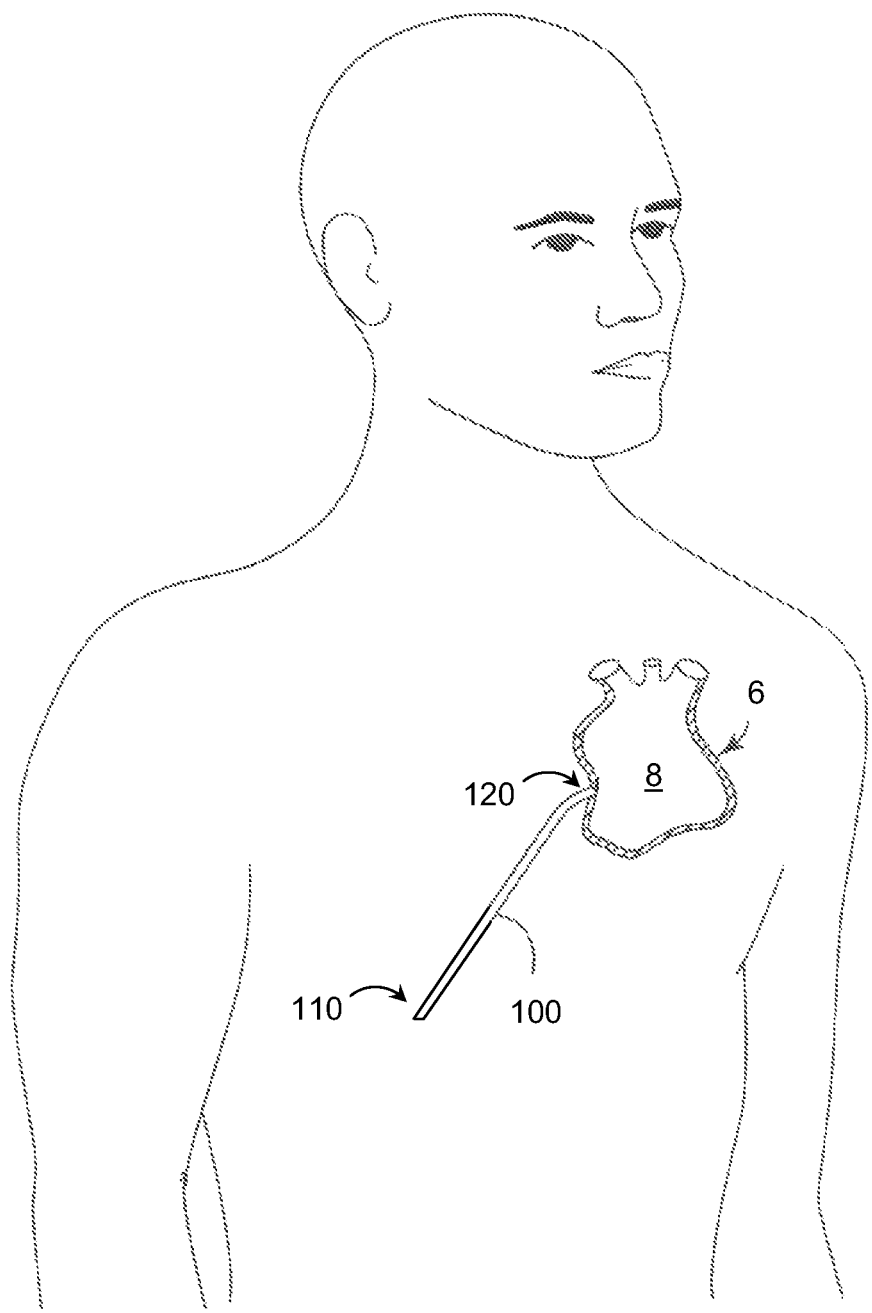
FIG. 1 is a schematic view of a partially implanted catheter in the environment of a patient.

Referring now to FIG. 1, a catheter 100 of a representative delivery system is schematically shown in the environment of a patient. The catheter 100 has a proximal end 110 and a distal end 120. In the depicted embodiment, the proximal end 110 of the catheter 100 exterior to the patient, and the distal end 120 is implanted in the patient at a target tissue location, in this case in the pericardial sac 6 of the heart 8. Biologic agents that are administered intravenously have a relatively short time for contacting cardiac tissue compared to agents delivered into the pericardium. Of course, in various embodiments, it may be desirable to deliver the agent intramyocardially, intracoronary or into the heart in any other suitable manner. While the catheter 100 in FIG. 1 is depicted as being implanted for delivery of an agent to the heart 8, it is contemplated that the delivery systems and methods described herein may be used to deliver agent to any suitable target tissue of a patient, including any suitable subcutaneous tissue, including brain parenchyma, spinal canal, perispinal tissue, cerebrospinal fluid, spleen, pancreas, stomach, intestine, kidney, liver, muscle, and the like.

Figure 2:
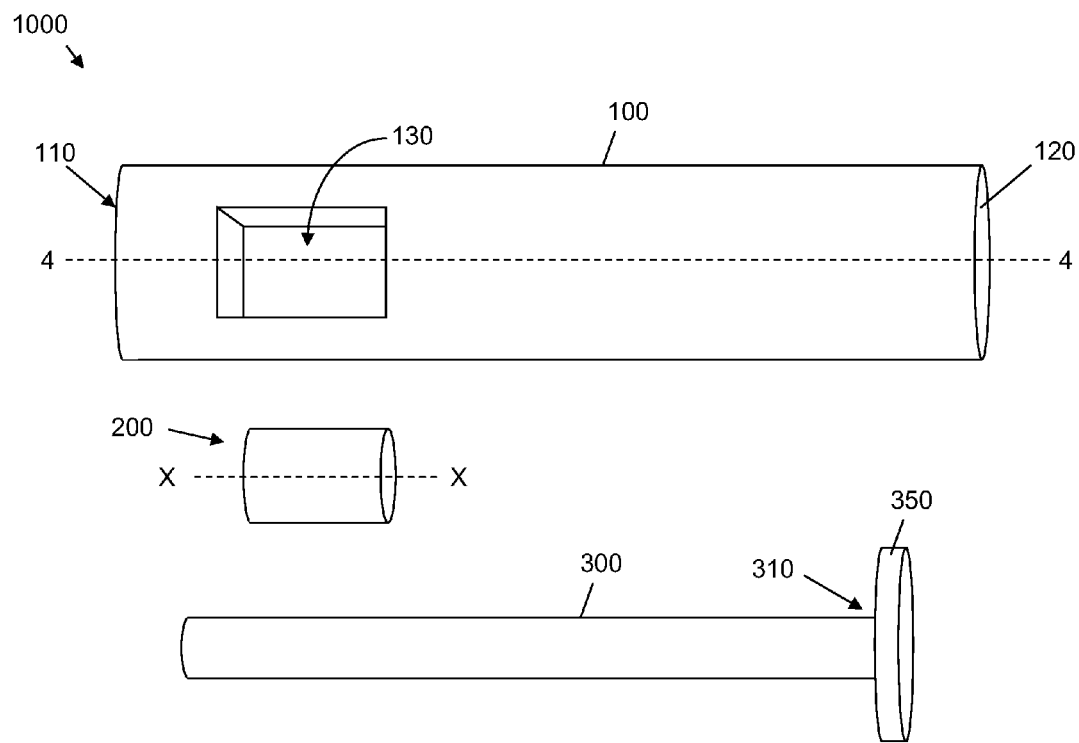
FIG. 2 is a schematic perspective view of a representative delivery system.
Figure 3:
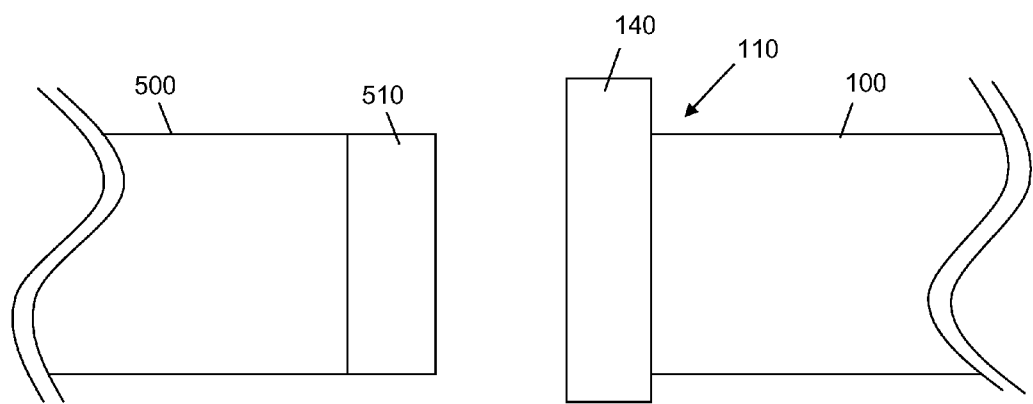
FIG. 3 is a schematic side view of a catheter and tube with complementary connector fittings.

Referring now to FIGS. 2-3, a schematic illustration of some representative components of a delivery system 1000 is shown. The depicted delivery system 1000 includes a catheter 100, a capsule or container 200 for housing a biologic agent, and a bar 300. The catheter 100 has a proximal end 110 and a distal end 120 and a body member defining a lumen that extends from the proximal end 110 to the distal end 120 of the catheter 100. The container 200 is configured to house a biologic agent and is insertable into the lumen of the catheter 100 and slidably disposable in the lumen. The bar 300 is also slidably disposable in the lumen of the catheter 100, as will be described in more detail below. In the embodiment depicted in FIG. 2, a pushing member 350 is coupled to the distal end 320 of the bar 300. The pushing member 350 may be integrally formed with, connected, attached, bonded, or otherwise coupled to the bar 300.

As shown in FIG. 2, an opening 130 is formed in the body of the catheter 100. The opening 130 forms a bore in the catheter 100. The bore intersects the lumen of the catheter 100 and is substantially perpendicular to the axis of the lumen. The opening 130 is configured to receive the container 200 such that the container 200 may be placed in the opening 130 to gain access to the catheter lumen. A cover (not shown) or other member may sealingly engage the opening 130. The cover or other member may be removed or opened to insert the container 200 into the opening 130, and replaced to sealingly engage the opening 130 after the container 200 is inserted in the opening. It will be understood, that when catheter 100 does not include such an opening 130 for receiving the container 200, the container 200 may be inserted into the catheter lumen via an opening at the proximal end 110 of the catheter, through which the lumen extends.

As shown in FIG. 3, the proximal end 110 of the catheter 100 may include a connection fitting 140 for sealingly coupling to tube 500 having a complementary connection fitting

510. The embodiment depicted in FIG. 3 may be desirable when hydraulics are use to control movement of the bar within the lumen of the catheter 100.

Figure 4A:
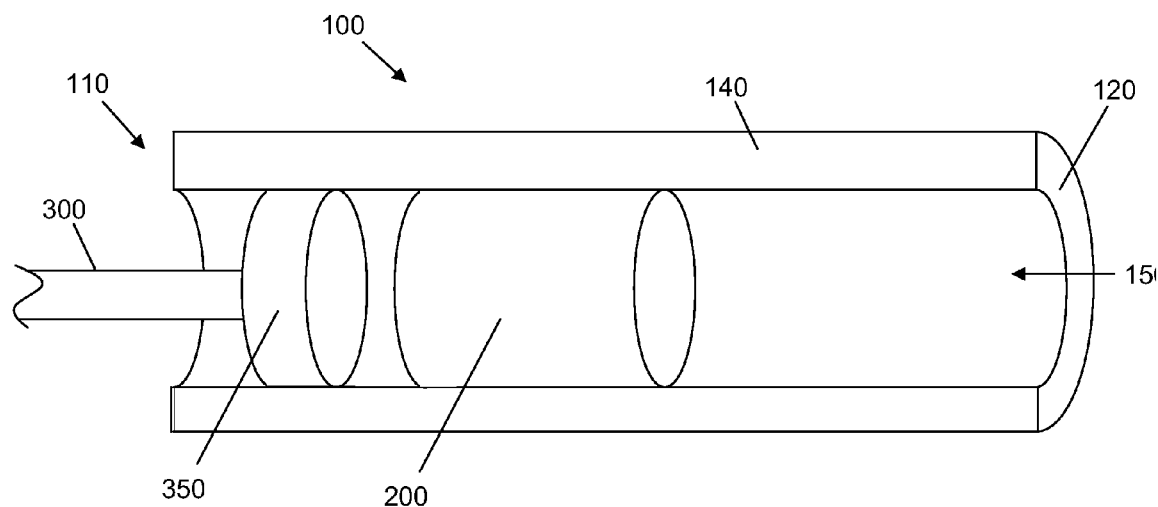
FIGS. 4A-D are schematic longitudinal cross sections of representative catheters.

Referring now to FIG. 4A, a schematic illustration of a cut away view of the catheter 100 shown in FIG. 2 (along line 4-4) with bar 300 and container 200 disposed within the lumen 150 is shown. Again, catheter 100 has a proximal end 110 and a distal end 120 and a body member 140 defining a lumen 150 extending from the proximal end 100 to the distal end 120. The container 200 and bar 300 are slidably disposable in the lumen 150. In the depicted embodiment, a pushing member 350 is coupled to the bar 300. The bar 300 and pushing member 350 are positioned in the lumen 150 of the catheter 200 such that the pushing member 350 is capable of engaging the container 200 and pushing the container 200 distally in the lumen 150 when the bar 300 is slid distally in the lumen 150.

Figure 4B:
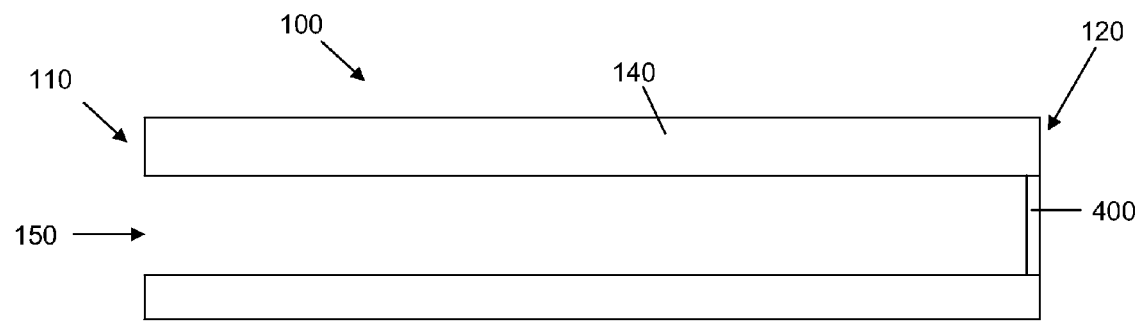
Figure 4C:
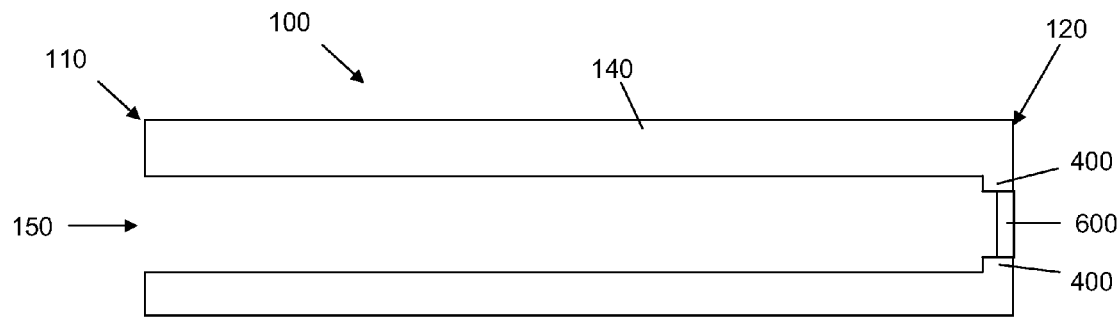
Figure 4D:
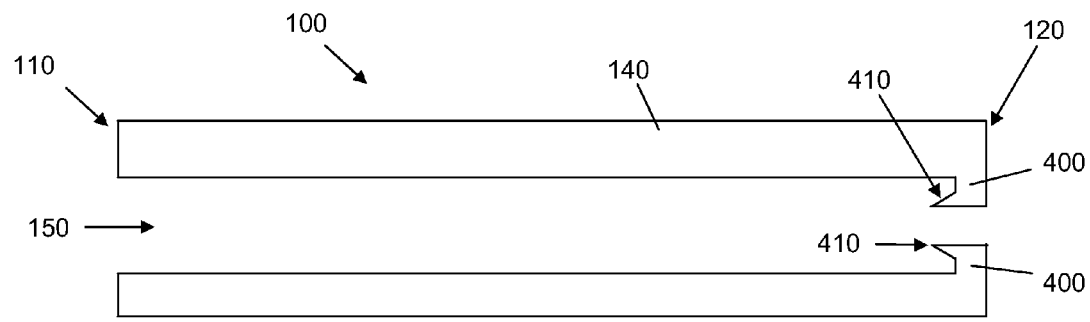

Referring now to FIGS. 4B-D, longitudinal cross sections of representative embodiments of catheters 100 are shown. For purposes of illustration, the sections can be considered as being taken along line 4-4 of the catheter 100 depicted in FIG. 2. The catheters 100 depicted in FIGS. 4B-D have a proximal end 110, a distal end 120, and a body member 140 defining a lumen 150 extending from the proximal end 110 to the distal end 120. A stop feature 400 is positioned in proximity to (e.g., at or near) the distal end 120 of the catheter 100. The stop feature 400 extends into the catheter lumen 150 and is configured to engage the container 200 to inhibit or prevent the container from exiting the lumen 150 at the distal end 120 of the catheter 100. It will be understood, as described below with regard to various embodiments, the stop feature 400 is intended to inhibit or prevent the entirety of the container 200 from exiting the lumen 150, as a portion of the container 200 may exit the lumen 150. The stop feature 400 may be integrally formed with, bonded to, adhered to, affixed to, or otherwise coupled to the body 140 of the catheter 100. As shown in FIG. 4D, a stop feature 400 may include a piercing element 410 positioned and configured to pierce the container, as described in more detail below with regard to various embodiments.

As shown in FIG. 4C, a filter 600 or screen may be disposed across the catheter lumen 150 in proximity to the distal end 120. The filter 600 or screen may prevent unintended particulate matter from exiting the lumen 150 into target tissue of a patient when the catheter is put to use. In the embodiment depicted in FIG. 4B, the stop feature 400 may serve as a filter or screen in addition to serving to inhibit or prevent the container from exiting the lumen.

A catheter as described herein may be made of any suitable material or combinations of material. For example, the body of the catheter may be formed from a suitable polymeric material, such as PTFE, ETFE, polyethylene, polypropylene, polycarbonate, or combinations of polymeric materials and may include reinforcing elements such as braids or meshes. In various embodiments, the catheter may be formed from silicone or polyurethane.

A catheter as described herein may have any suitable dimensions to carryout its intended therapeutic purpose. For example, the catheter is preferably long enough to allow its distal end to be implanted in a target tissue location and to allow its proximal end to be external to the patient. The diameter of the catheter lumen is sized to allow movement of a bar, pushing member if employed, and container within the lumen.

A bar as described herein may be made of any suitable material or combinations of material. When the catheter is flexible and follows a non-linear path through the body of a patient to the target tissue, the bar is preferably sufficiently flexible to follow the non-linear path within the catheter. However, for many therapies, the path that the catheter follows in the patient's body should be substantially linear. In such situations, the bar may be less flexible. In various embodiments, the bar is formed from silicone rubber, butyl rubber, fluorocarbon rubber, neoprene, polyurethane, polyethylene, polypropylene, polytetrafluoroethylene (PTFE), perfluoroalkoxy (PFA), fluorinated ethylene propylene (FEP), ethylene-propylene copolymers,polystyrene, polycarbonate, metals such as stainless steel or nitinol, glass or the like.

A pushing element as described herein may be made of any suitable material or combinations of material. For example, a pushing element may be formed from materials similar to those enumerated above with regard to the bar.

A piercing element as described herein may be made of any suitable material or combinations of material. In various embodiments, the piercing element is formed from a rigid polymeric material, such as polystyrene, high density polyethylene, polycarbonate, or the like.

A filter as described herein may be made of any suitable material or combinations of material. For example, a pushing element may be formed from materials similar to those enumerated above with regard to pushing member.

Figure 5A:
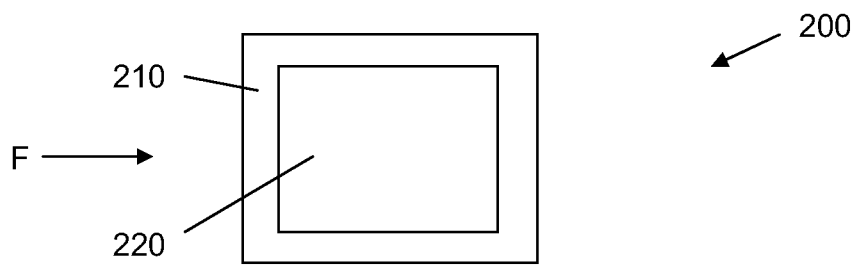
FIGS. 5A-B and 6A-B are schematic longitudinal cross sections of representative containers.

Referring now to FIGS. 5-6, schematic illustrations of cross sections of representative containers 200 are shown. In the embodiment depicted in FIG. 5A, the container 200 includes a housing 210 defining a reservoir 220 for containing a biologic agent. In various embodiments, the wall is formed from an elastomeric material and the volume of the reservoir 220 is variable. In numerous embodiments, the housing 210 is sufficiently stiff to maintain its shape to ensure proper slidability within a lumen of a catheter of a delivery system. Regardless of the degree of stiffness of housing 210, the container 200 is configured such that force applied to one face (e.g., in the direction of line F), or a portion thereof, of the container 200, while the opposing face is substantially stationary, causes the face on which force is exerted to move towards the opposing stationary face to force contents out of the reservoir. In various embodiments, the housing 210 is configured to be piercable by a piercable element, to allow contents of the reservoir 220 to escape, and in some embodiments, to reduce internal reservoir pressure so that such pressure does not overcome force F.

Figure 5B:
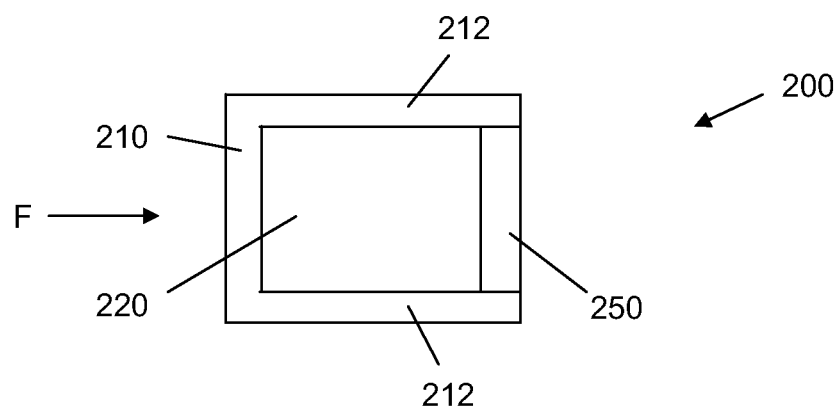

In the embodiment depicted in FIG. 5B, a rupturable membrane 250 sealingly engages the interior perimeter of a wall 212 of the housing 210 such that the rupturable membrane 250 and the housing together define the reservoir 220 for containing a biologic agent. While not shown, it will be understood that rupturable membrane 250 may sealingly engage an exterior perimeter of the wall 212. The membrane 250 may be bonded, adhered, affixed or otherwise attached or sealingly engaged to the wall 212. The rupturable membrane 250 may be piercable by a piercable element of a catheter of a delivery system, may rupture upon increased pressure (e.g., when force F is applied), may include a line of weakening along which the rupture may occur, or the like. In various embodiments, the rupturable membrane 250 is a self sealing septum that allows introduction of the biologic agent into the reservoir 220 via a needle (not shown) and sealingly contains the biologic agent upon withdrawal of the needle.

Figure 6A:
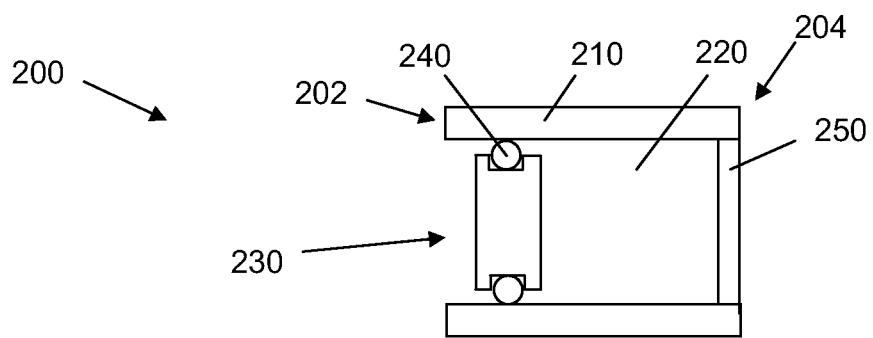
Figure 6B:
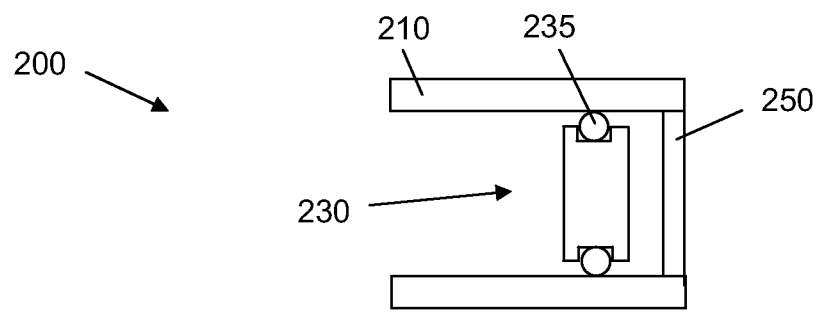

Referring now to FIGS. 6A-B, container 200 includes a body member 210 having a proximal end 202 and a distal end 204. The body member 210 defines a lumen extending from the proximal end 202 to the distal end 204. The container further includes a sealing element 230 slidably disposable within the lumen of the container 200. The sealing element 230 is configured to sealingly engage the body member 210 as the element 230 is slid within the lumen. In the depicted embodiment, the sealing element 230 includes an O-ring 235 for sealingly engaging the body member 210 within the lumen. Of course, sealing element 230 may form a seal in any suitable manner. For example, sealing member may include wiper seals or the like. A rupturable membrane 250 is disposed across the lumen in proximity to the distal end 204 of the body member 200. A reservoir 220 for containing a biologic agent is formed between the rupturable membrane 250, the sealing element 230 and the body member 210.

The housing of the container may be made of any suitable material. For example, the housing, or portions thereof, may be formed from, glass, silicanized stainless steel, silicanized titanium, nitinol, polystyrene, polyethylene, polycarbonate, ethylene vinyl acetate, polypropylene, polysulfone, polymethylpentene, polytetrafluoroethylene (PTFE) or compatible fluoropolymer, a silicone rubber or copolymer, poly(styrene-butadiene-styrene), polyurethane or the like, or a combination thereof. In various embodiments, the housing is made of polyurethane. It will be appreciated that the material of choice and thickness of the housing may be varied depending on the whether an elastic or rigid housing is desired.

Body (as shown in FIGS. 6A-B) may be formed of any suitable material. For example, body member may be formed of the same or similar materials as those described above with regard to a rigid housing.

Surfaces of the housing or other portions of a container that may come into contact with the biologic agent may be treated or coated to improve compatability with the biologic, reduce adherence of the biologic agent, or the like.

Rupturable membrane may be made of any suitable material, such as those enumerated above with regard to housing. In some embodiments, where rupturable membrane is a sealable septum, the membrane is made from a suitable elastomeric material, such as silicone rubber, butyl rubber, flurorcarbon rubber, polyethylene, polypropylene, polytetrafluoroethylene (PTFE) or the like. In many embodiments, the membrane is permeable to atmospheric gasses but is impermeable to aqueous liquids. In such embodiments, the membrane may be formed from polystyrene, polycarbonate, ethylene vinyl acetate, polysulfone, polymethylpentene, polytetrafluoroethylene (PTFE) or compatible fluoropolymer, a silicone rubber or copolymer, poly(styrene-butadiene-styrene), or polyolefin, such as polyethylene or polypropylene, or combinations of these materials. It will be understood that desired thickness may vary depending on the material from which the membrane is formed. By way of example, the membrane may be between about 0.02 millimeters and 0.8 millimeters thick.

Sealing member (moveable wall) may be formed from any suitable material. If the sealing member is a one-piece element formed from a single material, sealing member may be formed from a suitable elastomeric material, such as silicone rubber, butyl rubber, flurorcarbon rubber, neoprene, polyurethane, polyethylene, polypropylene, polytetrafluoroethylene (PTFE), perfluoroalkoxy (PFA), fluorinated ethylene propylene (FEP), ethylene-propylene copolymers, or the like If sealing element includes a separate sealing feature, such as an O-ring, wiper seal, or the like, the non sealing feature of the sealing element may be formed, for example, materials as enumerated above with regard to housing.

In various embodiments, the housing, sealing member, and rupturable membrane are all made of the same material to reduce the number of materials that the therapeutic agent contacts. For example, the housing, sealing member, and rupturable membrane may all be formed from polyurethane.

Referring now to FIGS. 7-11, longitudinal cross sections of some components of representative delivery systems 1000 are shown. In the various embodiments depicted in FIGS. 7-11, a container 200 is slidably disposed in a lumen 150 of a catheter 100. A bar 300 including a distally located pushing element 350 is slidably disposed in the lumen 150. The container 200 is positioned in the lumen 150 distally relative to the bar 300 and pushing element 350. As the bar 300, 500 is slid distally in the lumen 150, the pushing element 350, 550 engages the container 200 and causes the container 200 to slide distally in the lumen 150. Stopping feature(s) 400 located in proximity to (i.e., generally at or near) the distal end 120 of body member 140 inhibit or prevent container 200, or a portion thereof, from exiting the lumen 150 of the catheter 100. When the stop feature(s) 400 engage the container 200, further distal movement of bar 300, 500 in lumen forces the contents (not shown) of the container 200 out of the container 200 and out of the distal end of the lumen 150.

In the embodiment depicted in FIGS. 7A-D, piercing element 410 pierces a portion of the face of the container housing 210' facing the distal end 120 of the catheter body 140 as the container moves distally in the catheter lumen 150. Further distal movement of bar 300 in lumen 150 forces contents (not shown) out of the container 200 and out of the distal end of the lumen 150 through the pierced region. In addition, the side walls 210", 210''' of the container housing collapse as the bar is moved distally when the container 200 engages the stop feature 400 (see FIG. 7D). The side walls 210", 210''' may be in the form of a bellows, may be sufficiently deformable to collapse, or the like. In various embodiments (not shown), the piercing element 410 may be a needle advanced distally through the lumen 150 of the catheter 100 and through the container 200. For example, the needle (not shown) may be inserted through a lumen (not shown) of the bar 300. The needle may have an etched surface for piercing the container 200 or may have a surface that is covered with an array of microneedles to allow for more spreadout distribution of the agent.

Figure 7A:
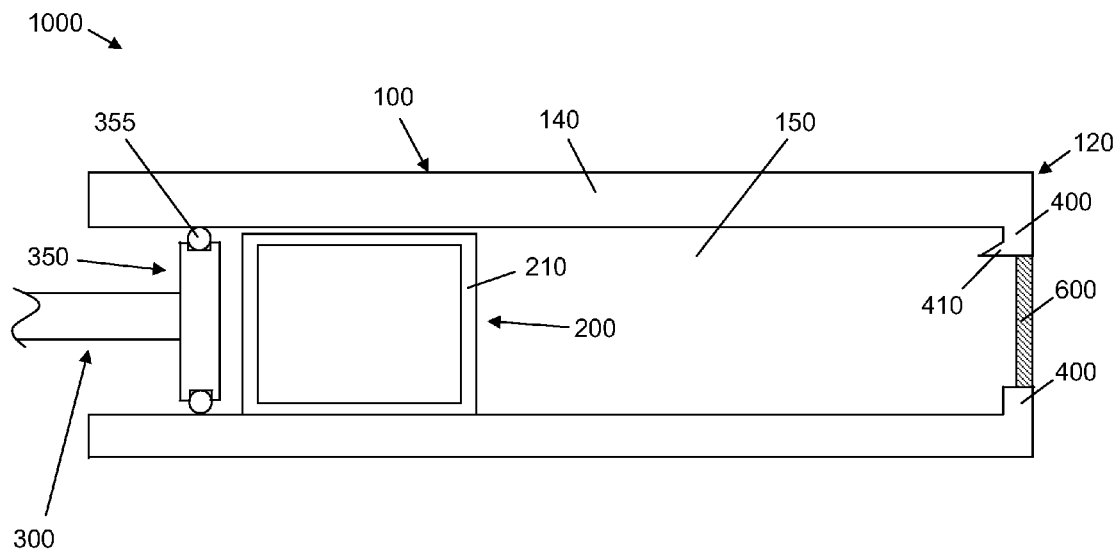
FIGS. 7A-D are schematic longitudinal cross sections of a first embodiment of a representative delivery system.
Figure 7B:
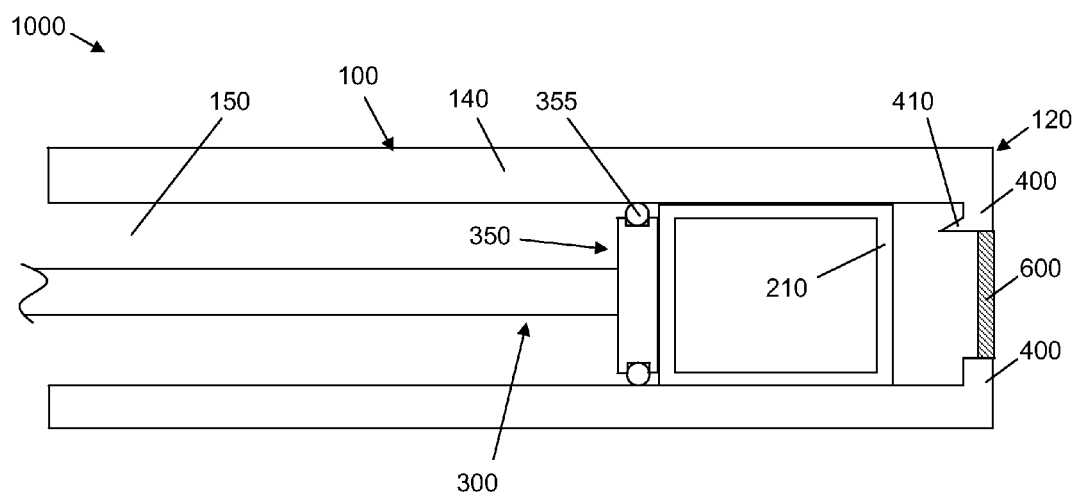
Figure 7C:
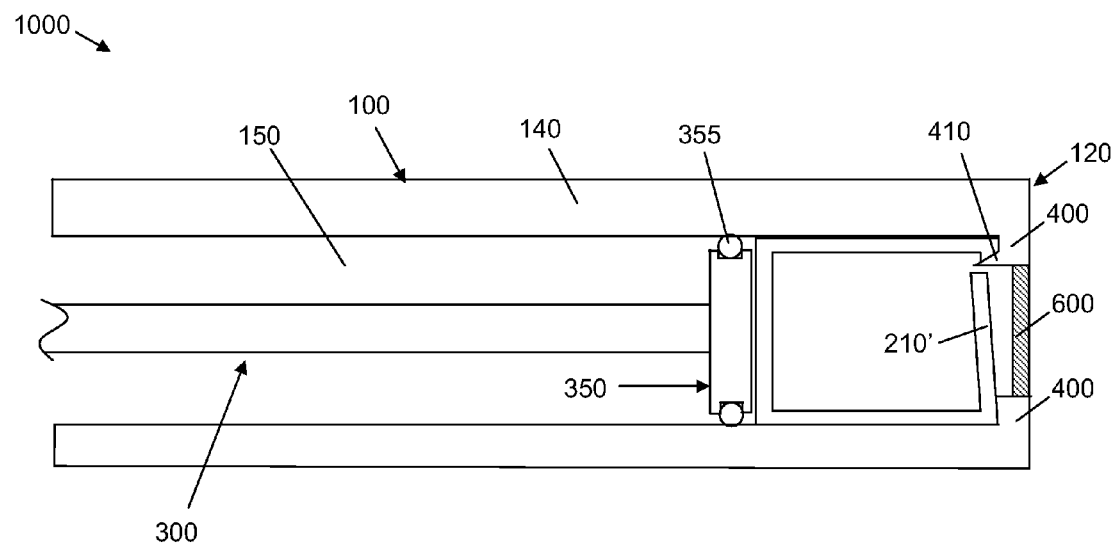
Figure 7D:
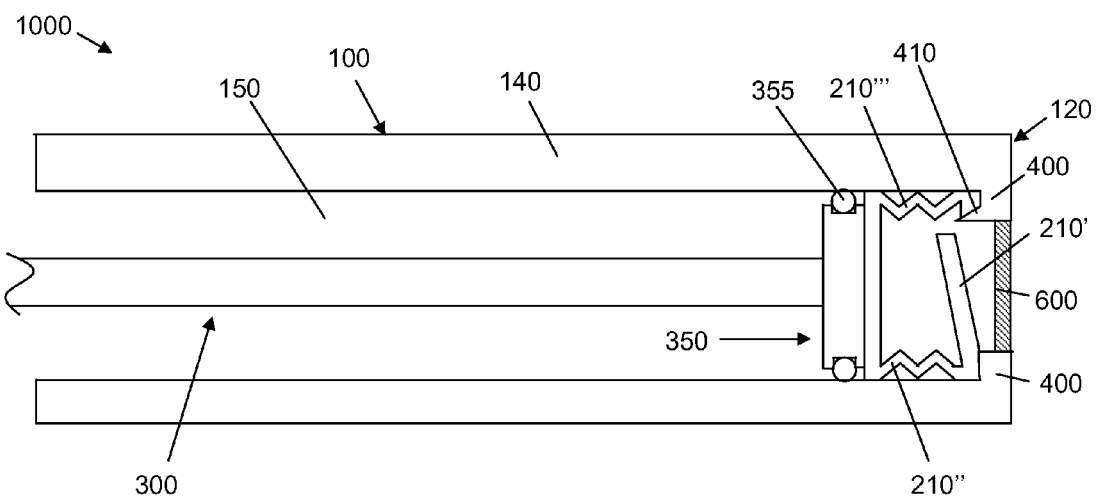

As further shown in FIG. 7D, a screen 600 or filter may be disposed in the catheter lumen 150 in proximity to the distal end 120 to inhibit or prevent unintended particulate matter, such as parts of the container housing 210, from exiting the lumen 150. As further shown in the embodiment depicted in FIGS. 7A-D, pushing element 350 includes a sealing element 355, such as an O-ring, so that pushing element 355 sealingly engages body 140 in lumen 150. By sealingly engaging body 140 in lumen 150, pushing element 350 can inhibit or prevent contents that leave container 200 from moving proximally in the lumen 150. In various embodiments, pushing element 350 does not sealingly engage body 140 of catheter 100.

Figure 8A:
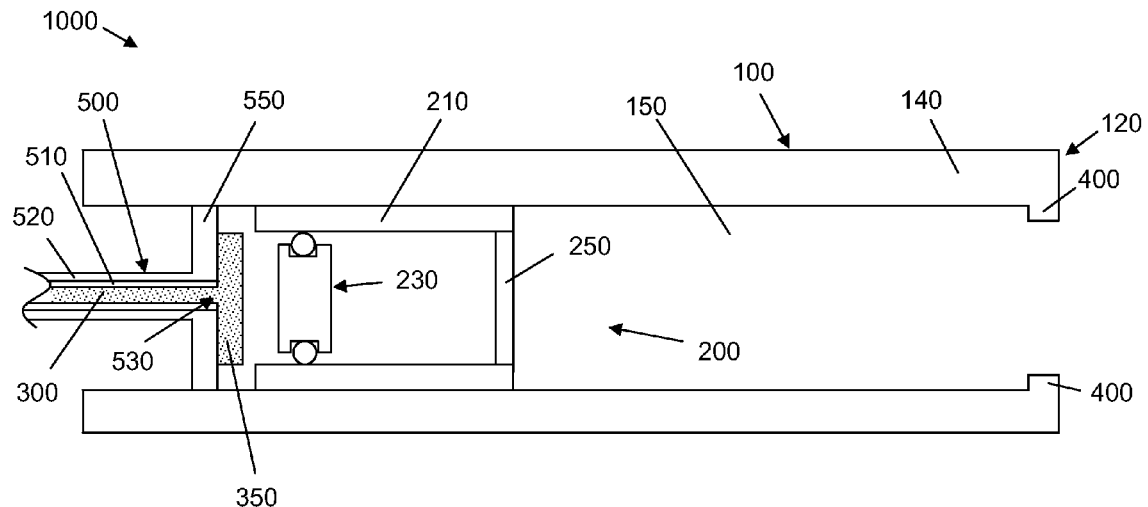
FIGS. 8A-C are schematic longitudinal cross sections of a second embodiment of a representative delivery system.
Figure 8B:
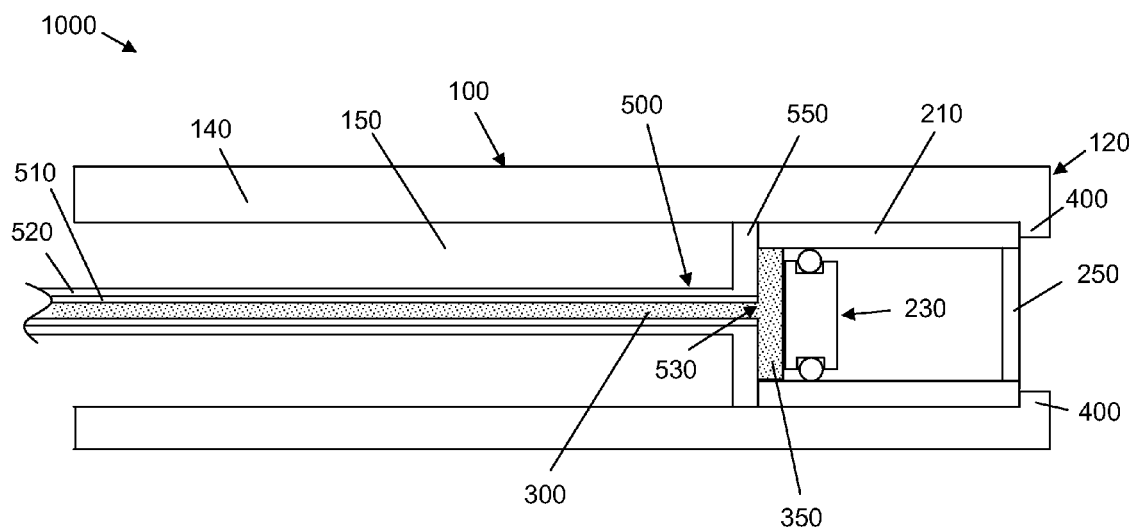
Figure 8C:
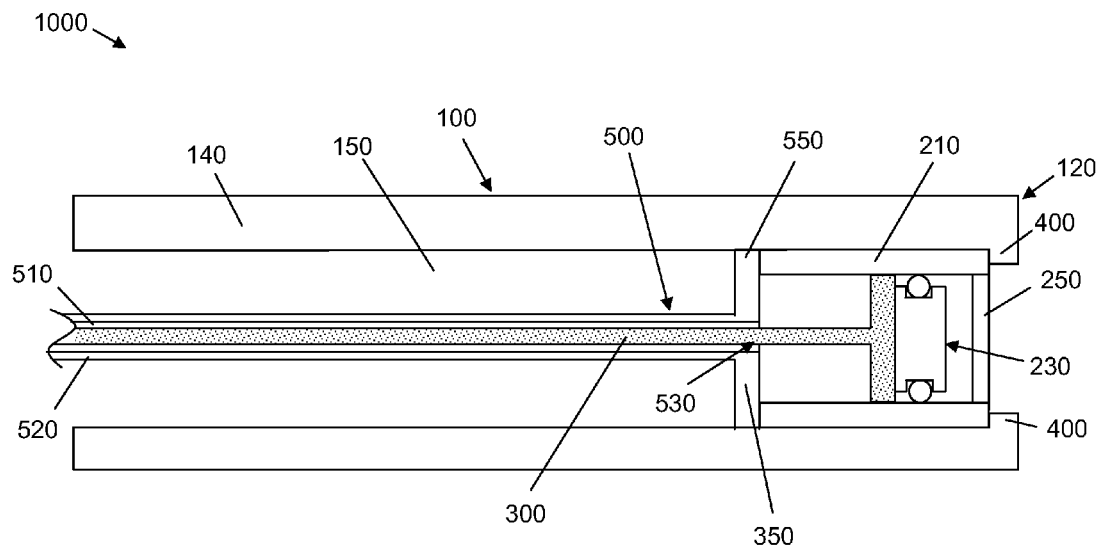

Referring now to FIGS. 8A-C, a container 200 similar to that depicted in and discussed with regard to FIGS. 6A-B is shown disposed in catheter lumen 200 distally to bar 300. The bar 300 is slidably disposed in lumen 510 a second bar 500, which is slidably disposed in the lumen 150 of the catheter 100. The second bar 500 includes a body member 520 that defines the lumen 510. The second bar 500 includes a pushing member 550 at the distal end of the bar 500. The second pushing member 550 includes an opening 530 axially aligned with the lumen 512. The first bar 300 is axially slidable in the lumen 510 of the second bar 500 and extendable beyond the opening 530. The second pushing member 550 is configured to engage the container 200 and move the container 200 distally in the catheter lumen 150 as the second bar 500 slides distally in the catheter lumen 150. The second bar 500 pushes the container 200 distally in the catheter lumen 150 until the container 200 engages stop feature 400. If the second bar 500 is moved manually within the catheter lumen 150, tactile feedback that the container 200 has engaged the stop feature 400 may indicate to the user that no further distal pushing of the bar 500 is desirable. If the bar 500 is moved via an automated mechanism, feedback, such as increased resistance to movement, increased pressure on stop feature, increased power consumption without further movement or the like may be used to indicate that further distal movement of the bar 500 should be ceased.

In the embodiment depicted in FIGS. 8A-C, distal movement of the second bar 500 causes distal movement of the first bar 300, as the second pushing element 550 engages the first pushing element 350 and pushes the first pushing element 350 distally as the second bar 500 is slid distally in catheter lumen 150. At a point where the second bar 500 is pushed distally such that the container 200 engages stop feature 400, the first bar 300 may be moved distally to force contents (not shown) out of the container 200 and out of the catheter 100. In the embodiment shown, the pushing element 350 of the first bar 300 is configured to engage the moveable sealing member 230 of the container 200. As the first bar 300 is moved distally when the container 200 is engaged with stop feature 400, the pushing element 350 moves the sealing member 230 distally forcing contents out of container 200 via rupturable membrane 250. While not shown, it will be understood that a filter or screen may be disposed across the catheter lumen 150 (e.g., as shown in FIGS. 7-D).

Figure 9A:
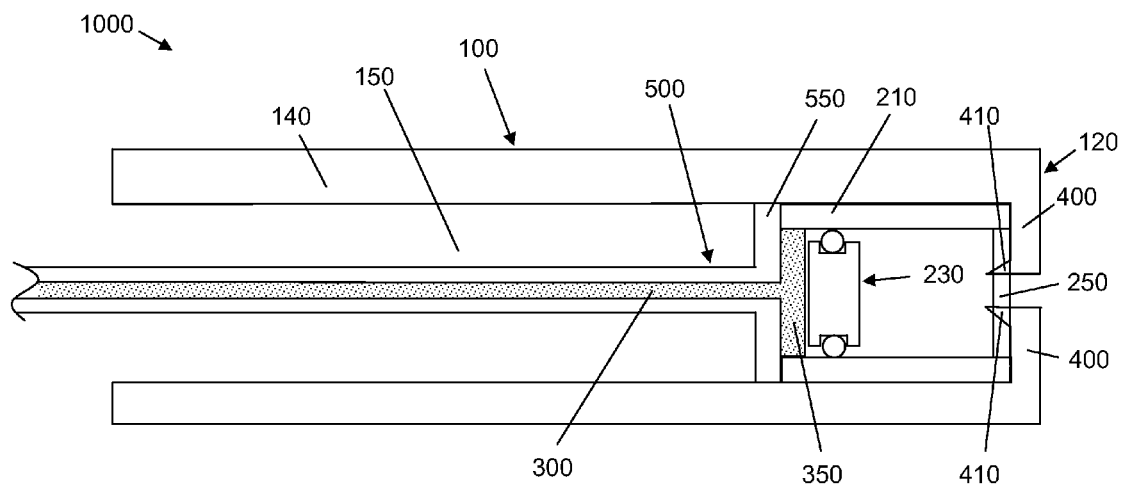
FIGS. 9A-B are schematic longitudinal cross sections of a third embodiment of a representative delivery system.
Figure 9B:
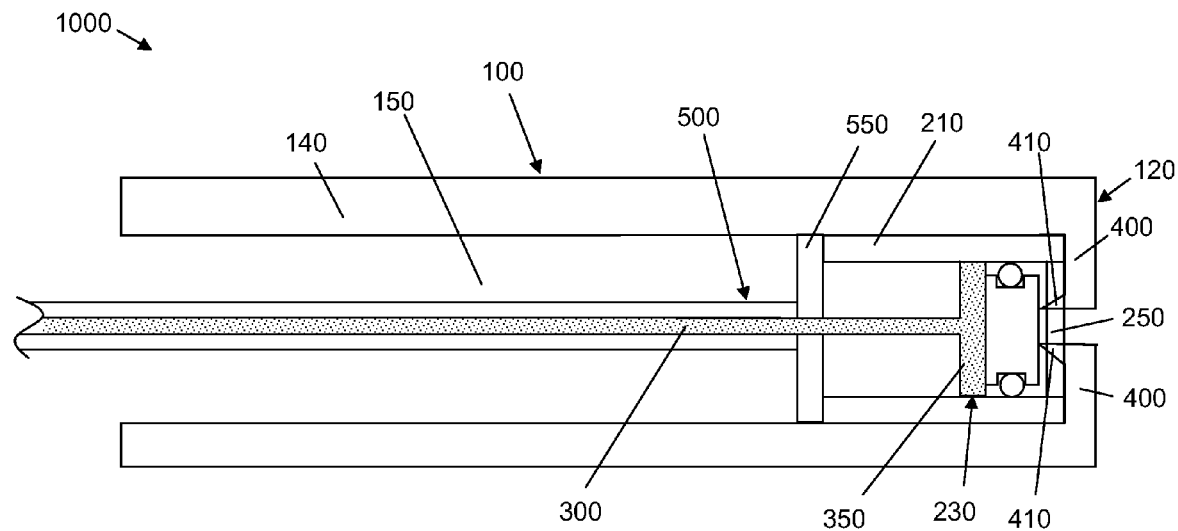

Referring now to FIGS. 9A-B, an embodiment similar to that shown in FIGS. 8A-C is shown, with like numbers referring to like parts. In the embodiment shown in FIGS. 9A-B, the stop feature 400 includes piercing elements 410. When the container 200 is pushed distally in catheter lumen 150 such that the container 200 engages the stop feature 400, piercing element 410 pierces rupturable membrane 250. As the sealing member 230 is moved distally, contents of the container 200 can exit via the pierced portion of the membrane 250.

Figure 10A:
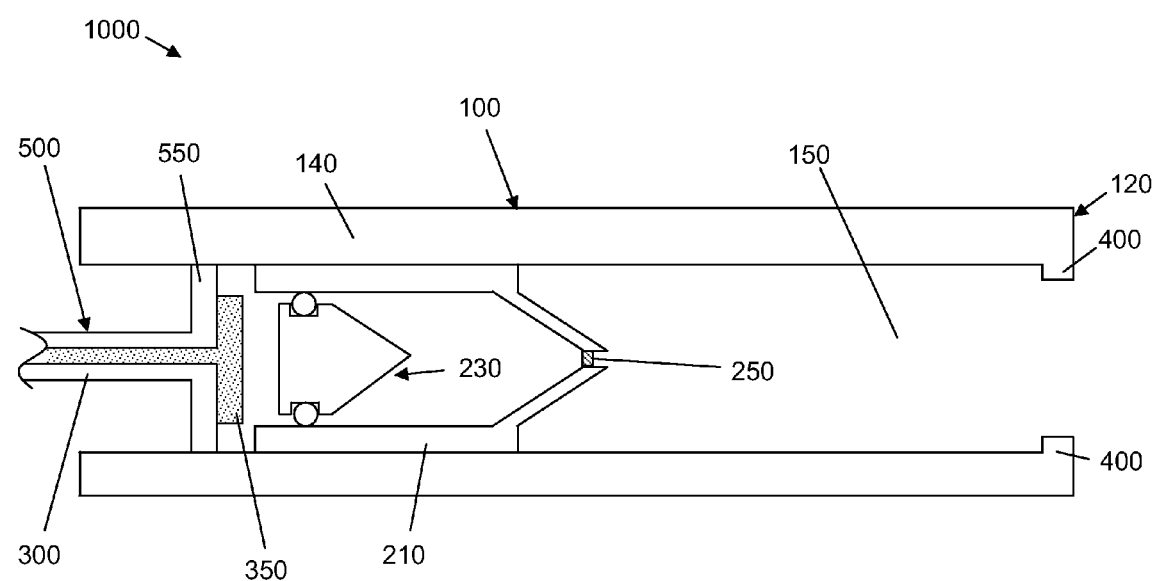
FIGS. 10A-C are schematic longitudinal cross sections of a fourth embodiment of a representative delivery system.
Figure 10B:
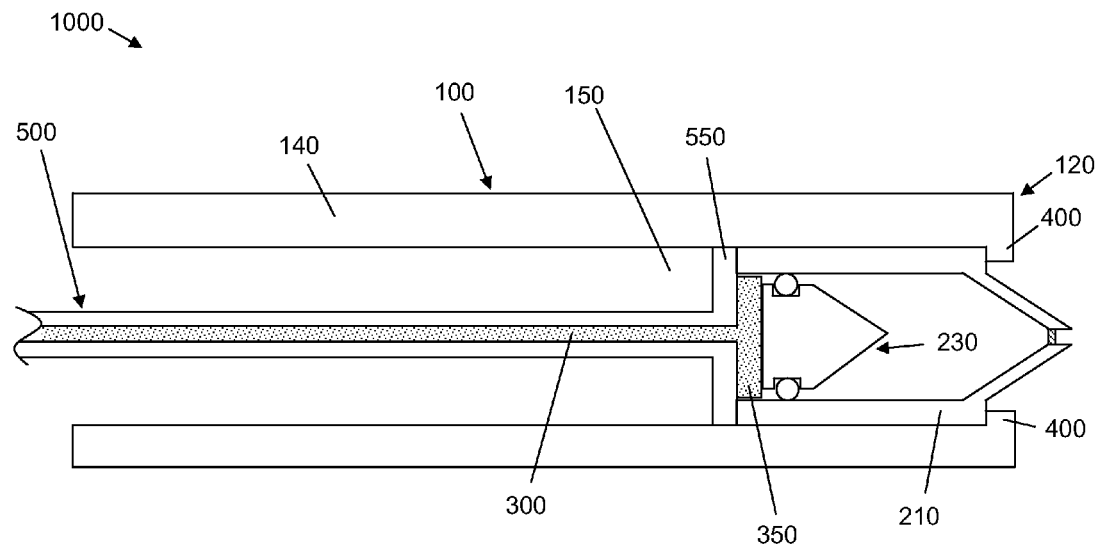
Figure 10C:
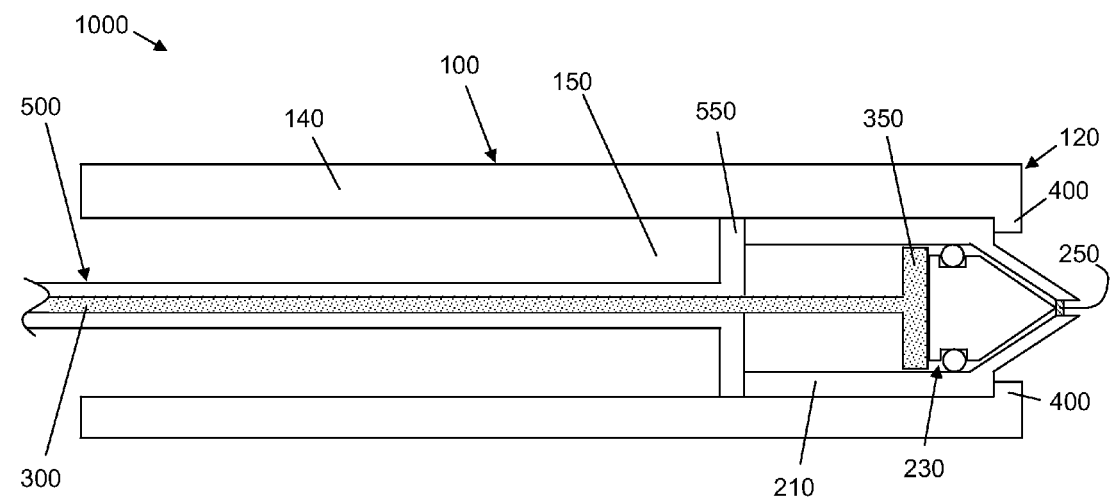

Referring now to FIGS. 10A-C, an embodiment similar to that shown in FIGS. 8A-C is shown, with like numbers referring to like parts. In FIG. 10, container 200 includes a tapered distal region configured to extend beyond the distal end 120 of the catheter 100 when the stop feature 400 engages the container 200. In various embodiments, the distal tapered region of the container 200 has a sufficiently large inner diameter to avoid subjecting the contents of the container 200 to shear stress as the contents are forced through the distal tapered region. As shown in FIG. 10, the sealing member 230 of the container 200 may be sized and shaped in a similar manner to the distal tapered region to increase the amount of contents that may be forced out of the container 200.

Figure 11:
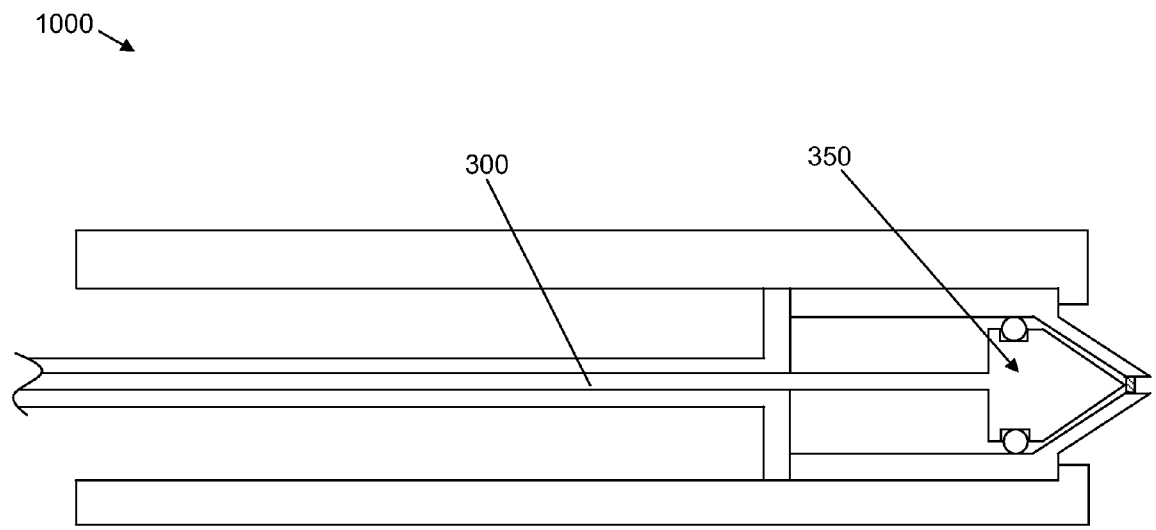
FIG. 11 is a schematic longitudinal cross section of a fifth embodiment of a representative delivery system.

Referring now to FIG. 11, a bar 300 or pushing member 350 of the bar may serve as a sealing member of a container. In the depicted embodiment, pushing member 350 sealingly engages the body of the container as the pushing member 350 is moved distally within the container to force contents out of the container.

While not shown, it will be understood that mechanisms other than bars 300, 500 may be used to move container 200 distally in lumen 150 and force contents out of the container 200. For example, air pressure or hydraulic fluid pressure (e.g., saline) may be used to move the container 200 and provide force to release contents. In such embodiments, it may be desirable for the container 200 to sealingly engage the body 140 of the catheter 100. It will be further understood that a bar 300, 500 may be moved in the lumen 150 by any suitable mechanism, such as hydraulic fluid pressure, air pressure, motor, manually, or the like.

Figure 12:
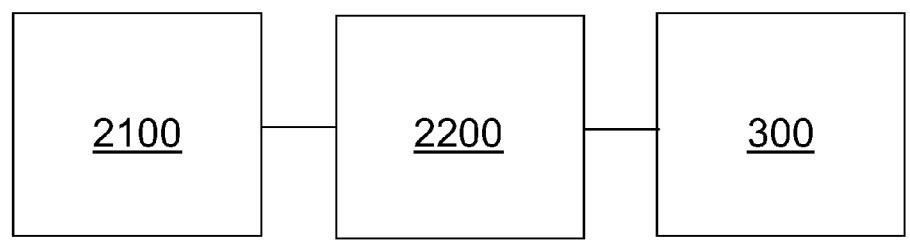
FIG. 12-14 are block diagrams of representative components of control and drive systems of representative delivery systems
Figure 13:
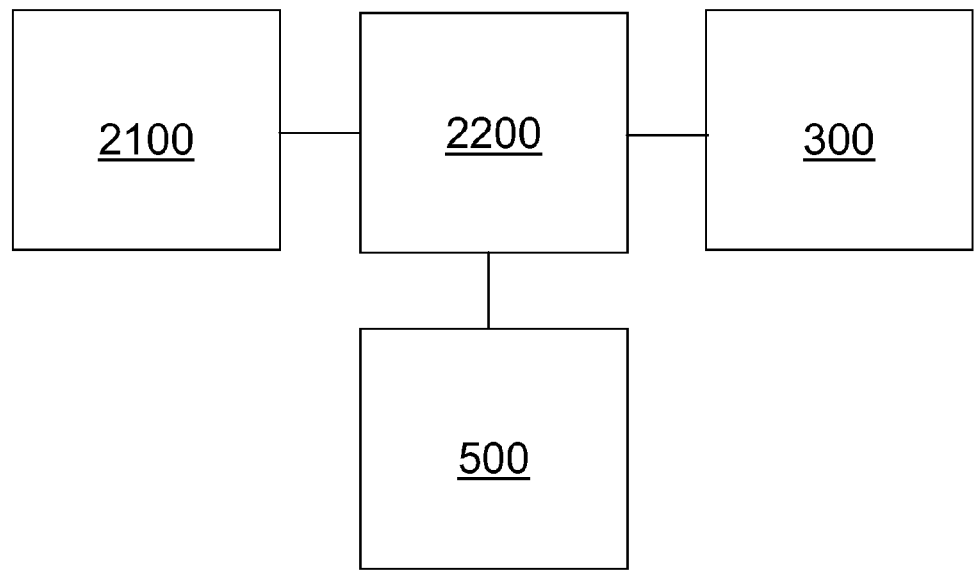
Figure 14:
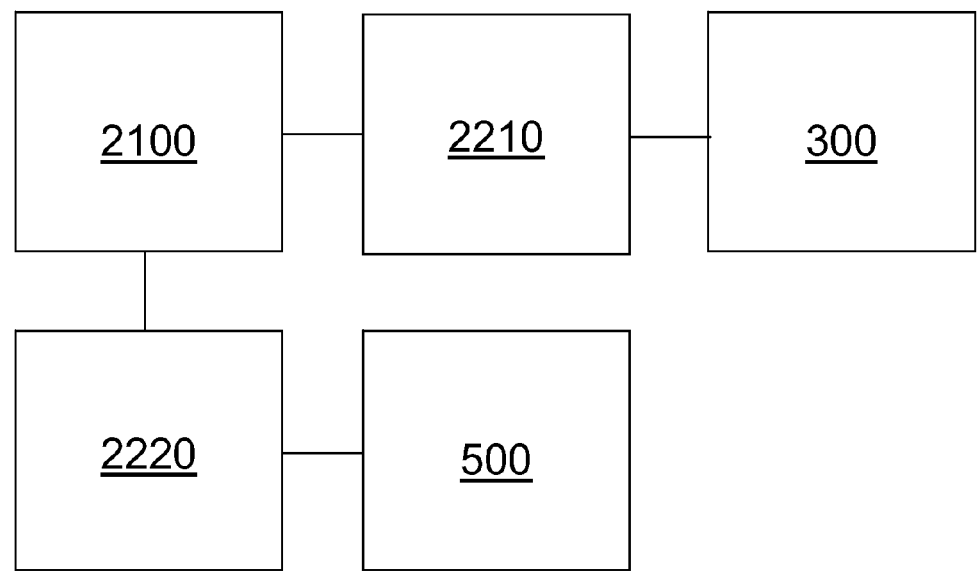

Referring now to FIGS. 12-14, block diagrams of some representative components of automated systems for moving bars as discussed above within lumens of catheters are shown. In the simple form shown in FIG. 12, such a system may include a controller 2100, a driving mechanism 2200, and a bar 300. Any suitable controller 2100, such as a microprocessor, may be employed to control the driving mechanism 2200. Any suitable driving mechanism 2200 may be employed to move bar 300. In various embodiments, the driving mechanism 2200 is a motor, such as a stepper motor. In some embodiments, the driving mechanism 2200 is a hydraulic or air pressure driving mechanism. In such embodiments, the bar 300 preferably sealingly engages the body of the catheter to prevent hydraulic fluid from leaking in the lumen distal to the bar 300. As shown in FIGS. 13-14, in embodiments where first 300 and second 500 bars are employed, a single drive mechanism 2200 may be used to drive both bars 300, 500 or a first drive mechanism 2210 may be used to move the first bar 300 and a second drive mechanism 2220 may be used to move the second bar 500.

Figure 15:
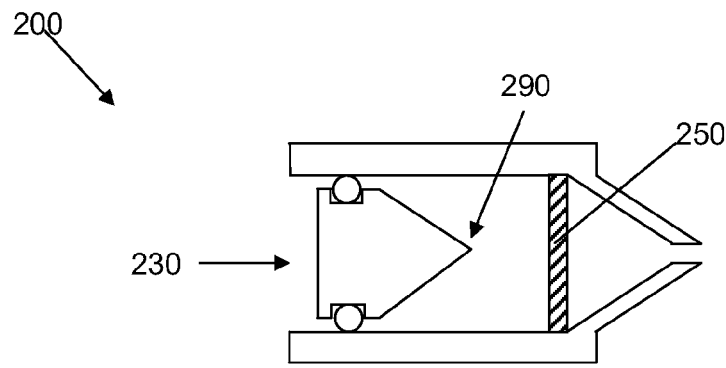
FIG. 15 is a schematic longitudinal cross section of a representative container.
Figure 16:
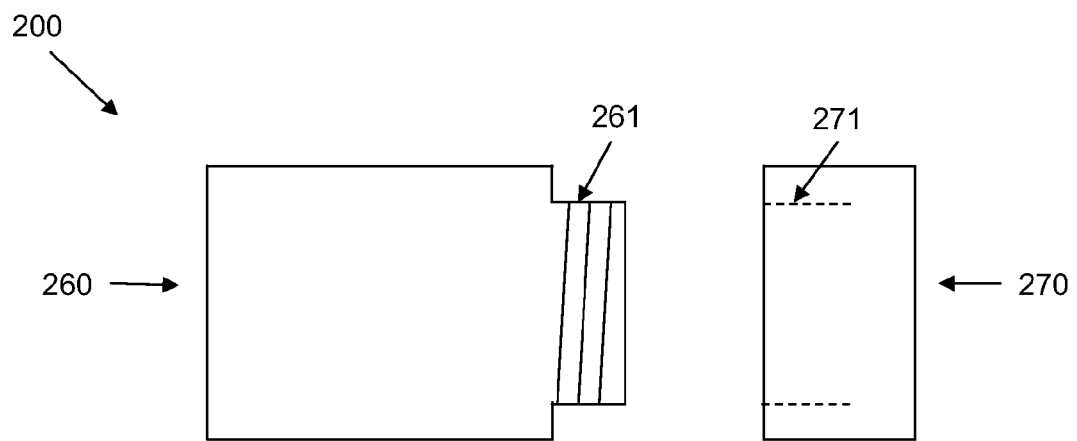
FIGS. 16 and 17A are schematic side views of representative two-part containers.
Figure 17A:
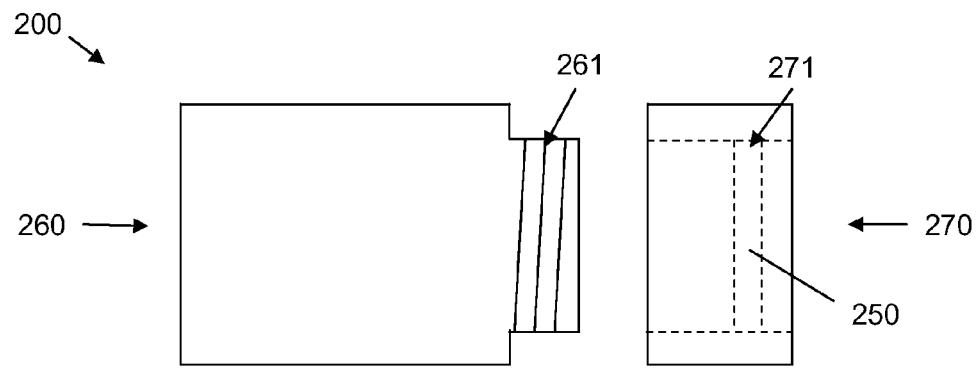
Figure 17B:
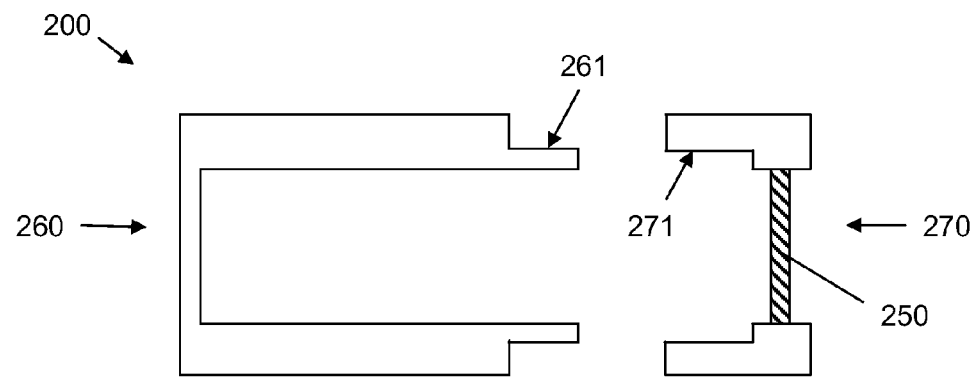
FIG. 17B is a schematic longitudinal cross section of the container depicted in FIG. 17A.
Figure 18:
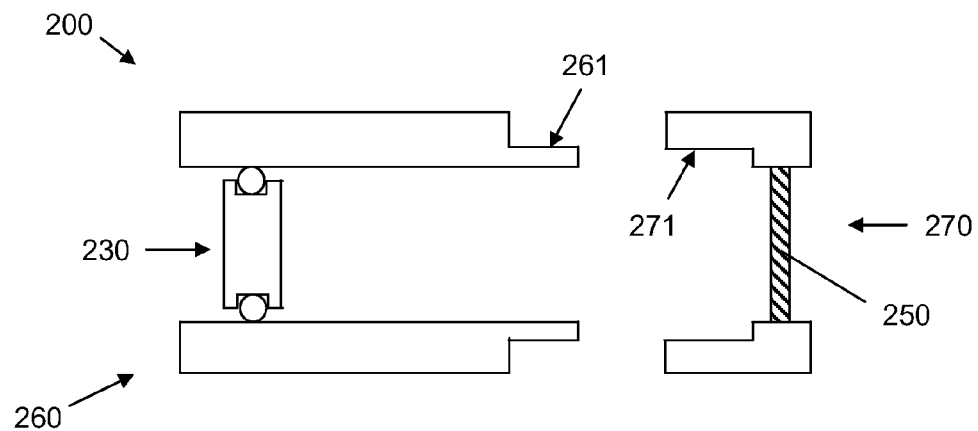
FIGS. 18-19 are schematic longitudinal cross sections of representative containers.

Referring now to FIGS. 15-22, schematic illustrations of various configurations of containers 200 useful in delivery systems as described above are shown. In FIG. 15, a schematic longitudinal cross section of a container 200 is shown. The container 200 includes a sealing element 230 and a rupturable membrane 250. The rupturable membrane 250 may be a self sealing septum to allow contents to be added to the container 200. The sealing element 230 includes a piercing element 290 configured to pierce rupturable membrane 250 to allow contents to exit the container 200 when the sealing member 230 is moved distally. As shown in the schematic side view of FIG. 16, a container 200 may include first 260 and second 270 connectable portions. The second portion 270 may serve as a removable and resealable cap. The cap may be removed so that contents may be added to the first portion 260 and resealed to prevent the contents of the container 200 from leaking or spilling. The first 260 and second 270 portions include complementary mating features 261, 271 to allow disconnecting and reconnecting of the first and second parts. In the depicted embodiment, the first portion 260 includes external threads 261. The second portion 270 includes complementary internal threads 271 (represented by internal dashed lines). Of course, any other suitable form of connection may be employed. As shown in FIGS. 17A-B, which is similar to the embodiment depicted in FIG. 16 with like numbers referring to like parts, the second portion 270 of the container 200 may include a rupturable membrane 250. In the embodiment depicted in FIG. 18, the first part 260 includes a sealing element 230 and the second part 270 includes a rupturable membrane 250.

Figure 19:
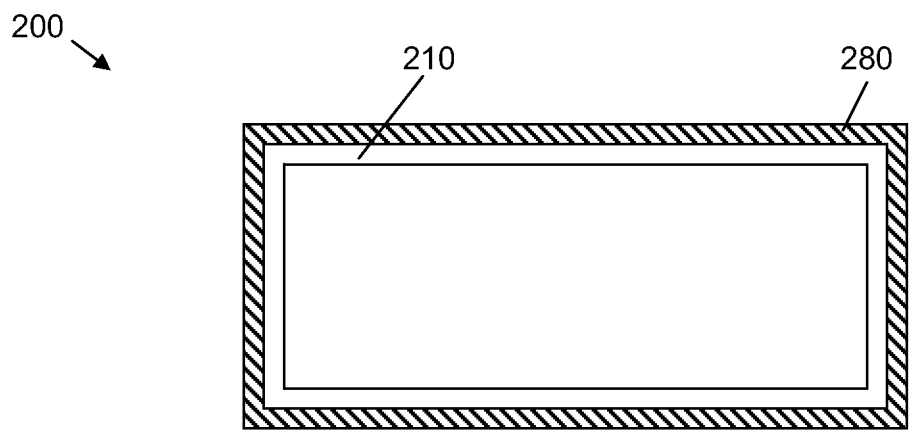

Referring now to FIG. 19, container 200 may include an outer sheath 280 that surrounds the housing 210 of the container. In various embodiments, the outer sheath 280 may be removed in the operating room prior to insertion of the container 200 into the lumen of a catheter of a delivery system. The sheath 280 may thus prevent excessive exposure (and thus contamination) of the housing 210 prior to delivery of its contents. In some embodiments, the outer sheath 280 may be removable following insertion into the catheter so that physician contact with the inner housing 210 is prevented. Of course, the outer sheath 280 and housing 210 may be ruptured in proximity to the distal end of the catheter as the agent disposed in the housing is released. In various embodiments, the outer sheath 280 is permeable to atmospheric gases, but impermeable to aqueous liquids. Such breathable outer sheaths 280 may be desirable when the container 200 houses cells and it is desirable to preserve the viability of the cells prior to delivery.

Figure 20:
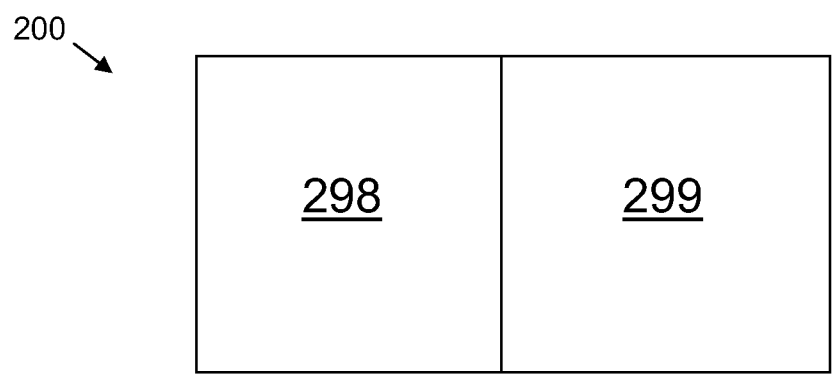
FIG. 20 is a block diagram of a container having two chambers.
Figure 21:
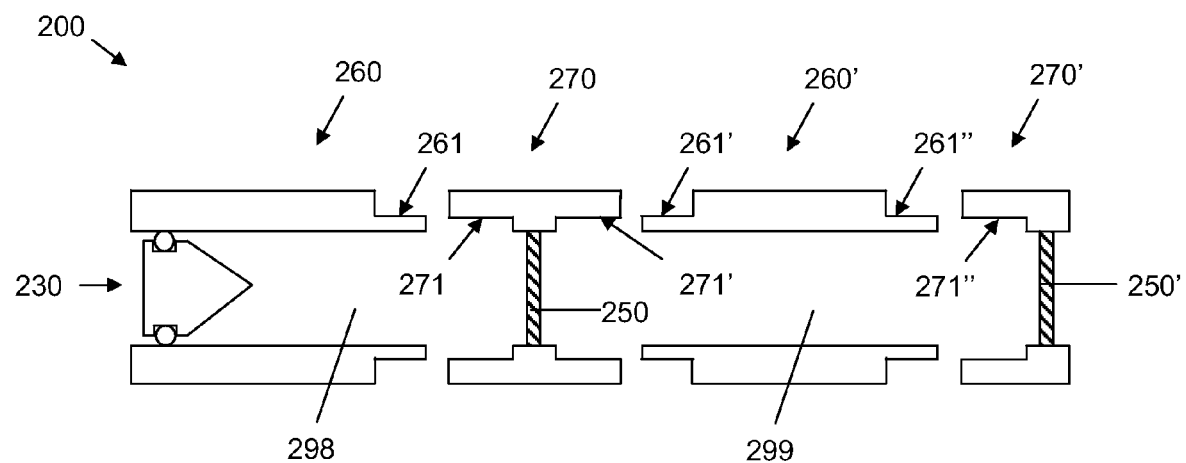
FIGS. 21-22 are schematic longitudinal cross sections of representative multi-part containers capable of forming two chambers.
Figure 22:
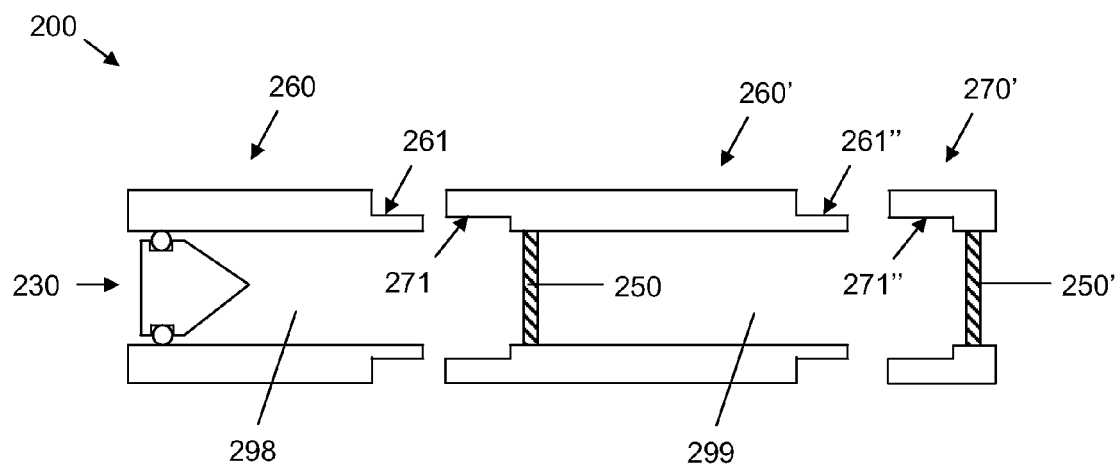

Referring now to FIG. 20, a container 200 may be sealingly subdivided into first 298 and second chambers 299. The first 298 and second 299 chambers may house different agents that may not be compatible if stored together. In various embodiments, the first chamber 298 houses a fluoroscopic medium to enable visualization via imaging techniques and the second chamber 299 houses a biologic agent. Just prior to introduction into a patient through the use of a delivery system as described above, the contents of the first 298 and second 299 chambers may be mixed. FIGS. 21-22 depict schematic longitudinal cross sections of two embodiments of such two-compartment containers.

In the embodiment depicted in FIG. 21, the container 200 includes first 260, second 270, third 260' and fourth 270' parts. The first 260 and second 270 parts include complementary mating features 261, 271 to allow for disconnection and sealing reconnection. The first 260 and second 270 parts together form the first chamber 298 of the container 200. A first material may be disposed in the first part 260 and the second part 270 may be connected to the first part 260 to seal the material in the first chamber 298. A rupturable membrane 250 prevents the material from exiting the sealed first chamber 298. The third part 260' includes a complementary mating feature 261' to a mating feature 271' of the second part 270 to allow for disconnection and sealing reconnection. The second 270, third 260', and fourth 270' parts together form the second chamber 299. The third part 260' includes a complementary mating feature 261" to a mating feature 271" of the fourth part 270' to allow for disconnection and sealing reconnection. When the second 270 and third 260' parts are connected, a second material may be introduced in the third part 260'. The fourth part 270' may then be sealingly connected to the third part 260'. The fourth part 270' includes a rupturable membrane 250' to prevent the contents of the second chamber 299 from leaking or spilling. The rupturable membrane 250 prevents interaction between the contents of the first 298 and second 299 chambers during storage. Upon rupture of the membrane 250 in use, the contents of the first 298 and second chambers 299 can mix.

In the embodiment depicted in FIG. 22, the container 200 includes first 260, second 260', and third 270' parts. The first 260 and second 260' parts include complementary mating features 261, 271 to allow for disconnection and sealing reconnection. The first 260 and second 270 parts together form the first chamber 298 of the container 200. A first material may be disposed in the first part 260 and the second part 270 may be connected to the first part 260 to seal the material in the first chamber 298. A rupturable membrane 250 prevents the material from exiting the sealed first chamber 298. The third part 270' includes a complementary mating feature 271' to a mating feature 261' of the second part 260' to allow for disconnection and sealing reconnection. The second 260' and third 270' parts together form the second chamber 299. A second material may be introduced in the second part 260'. The third part 270' may then be sealingly connected to the second part 260'. The third part 270' includes a rupturable membrane 250' to prevent the contents of the second chamber 299 from leaking or spilling. The rupturable membrane 250 prevents interaction between the contents of the first 298 and second 299 chambers during storage. Upon rupture of the membrane 250 in use, the contents of the first 298 and second chambers 299 can mix.

In the embodiments depicted in FIGS. 21-22, the moveable sealing member includes a tapered distal region that may serve as a piercing element to facilitate rupturing membranes 250, 250'.

While not described at length herein, it will be understood that the biologic agent to be delivered may be delivered in any form, e.g. liquid or solid. By using a system as described herein, solid forms and liquid forms of the biologic agent should be readily interchangeable without the need to design and develop new catheters or components of the system. Examples of suitable solid forms of biologics that may be delivered in accordance with the teachings provided herein include lyophilized particles or solid scaffolds. In many circumstances, solid scaffolds are considered more effective for delivering therapy to a highly vascularized region such as the myocardium.

The various embodiments shown and described herein include various components. One of skill in the art will readily understand that components of a given described embodiment may be readily substituted for, or used in addition to, components of a different described embodiment.

Thus, embodiments of the SYSTEM AND METHOD FOR DELIVERY OF BIOLOGIC AGENTS are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for delivering a therapeutic agent to a patient, comprising:
   a flexible catheter configured to follow a non-linear path through the patient, the catheter having a proximal end and a distal end and comprising a body defining a lumen extending from the proximal end to the distal end of the catheter;
   a container for housing the therapeutic agent, the container being insertable and slidably disposable in the lumen of the catheter;
   a first bar slidably disposable in the lumen, wherein sliding the first bar distally in the lumen forces the therapeutic agent out of the container and out of the lumen when the container is in proximity to the distal end of the catheter; and
   a filter disposed across the entire width of the catheter lumen in proximity to the distal end of the catheter body, the filter being configured to allow the therapeutic agent to exit the lumen and to prevent unintended particulate matter from exiting the lumen.

2. The system of claim 1, further comprising a stop feature in proximity to the distal end of the catheter, wherein the container is configured to engage the stop feature, wherein the distal movement of the first bar in the lumen forces the therapeutic agent out of the container and out of the lumen when the container is engaged with the stop feature and wherein the stop feature is configured to inhibit the container from exiting the lumen.

3. The system of claim 2, further comprising a first pushing member coupled to a distal end of the first bar, wherein the first pushing member is configured to engage the container and to force the therapeutic agent out of the container when the container is engaged with the stop feature as the first bar slides distally in the catheter lumen.

4. The system of claim 3, wherein the first pushing member is configured to engage the container and to move the container distally in the catheter lumen as the first bar slides distally in the catheter lumen.

5. The system of claim 2, further comprising a second bar having a body member, wherein the body member comprises a second bar lumen configured to receive the first bar,
wherein the first bar is axially slidable within the second bar lumen, and
wherein distally sliding the second bar in the catheter lumen causes the container to move distally in the catheter lumen.

6. The system of claim 5, further comprising a second pushing member coupled to a distal end of the second bar, wherein the second pushing member is configured to engage the container and to move the container distally in the catheter lumen as the second bar slides distally in the catheter lumen.

7. The system of claim 6, wherein the second pushing member forms an opening, wherein the second pushing member is coupled to the second bar such that the opening is axially aligned with the second bar lumen, and wherein the first bar is slidable in the second bar lumen and extendable beyond the opening of the second pushing member.

8. The system of claim 7, further comprising a first pushing member coupled to a distal end of the first bar, wherein the first pushing member is configured to engage the container and to force the therapeutic agent out of the container when the container is engaged with the stop feature as the first bar slides distally in the second bar lumen.

9. The system of claim 8, wherein the first pushing member has a diametric dimension greater than the diametric dimension of the opening of the second pushing member, and wherein the first pushing member is configured to prevent proximal sliding of the first bar in the second bar lumen when the first pushing member contacts the second pushing member.

10. The system of claim 2, further comprising a piercing element in proximity to the distal end of the catheter, wherein the piercing element protrudes into the catheter lumen and is configured to pierce the container as the container is moved distally in the catheter lumen.

11. The system of claim 2, wherein the filter element is the stop feature.

12. The system of claim 2, wherein the container comprises a sealing member distally moveable in the container.

13. The system of claim 12, wherein distal sliding of the first bar in the catheter lumen is configured to cause the sealing member to move distally when the container engages the stop feature.

14. The system of claim 12, wherein the first bar and the container are positionable within the catheter lumen such that the first bar engages the moveable sealing member upon sliding the first bar distally in the catheter lumen and causes the moveable sealing member to move distally relative to the catheter lumen and force the therapeutic agent out of the container and out of the lumen when the container is engaged with the stop feature.

15. The system of claim 2, wherein the container is formed from an elastomeric material.

16. The system of claim 2, wherein the container comprises a collapsible wall that is configured to collapse when the first bar is slid distally in the catheter lumen and the container engages the stop feature.

17. The system of claim 16, wherein the container comprises a resealable septum.

18. The system of claim 2, wherein the container comprises a resealable septum.

19. The system of claim 2, wherein the container comprises a membrane configured to be substantially impermeable to aqueous liquid and substantially permeable to atmospheric gasses, wherein the membrane is configured to allow exchange of gasses between the contents of the container and the exterior of the container and to prevent contents of the container from exiting the container under storage conditions.

20. The system of claim 2, wherein the container comprises a rupturable membrane configured to prevent contents of the container from exiting the container under storage conditions, but to allow release of the contents in use in the delivery system upon rupture of the membrane.

21. The system of claim 2, wherein the stop feature is integrally formed with the catheter.

22. A system for delivering a therapeutic agent to a patient, comprising:
a flexible catheter configured to follow a non-linear path through the patient, the catheter having a proximal end and a distal end and comprising a body defining a lumen extending from the proximal end to the distal end of the catheter;
a container for housing the therapeutic agent, the container being insertable and slidably disposable in the lumen of the catheter;
a first bar slidably disposable in the lumen, wherein sliding the first bar distally in the lumen forces the therapeutic agent out of the container and out of the lumen when the container is in proximity to the distal end of the catheter; and
a filter disposed across the catheter lumen in proximity to the distal end of the catheter body, the filter being configured to allow the therapeutic agent to exit the lumen and to prevent unintended particulate matter from exiting the lumen.

23. The system of claim 22, further comprising a stop feature in proximity to the distal end of the catheter, wherein the container is configured to engage the stop feature, wherein the distal movement of the first bar in the lumen forces the therapeutic agent out of the container and out of the lumen when the container is engaged with the stop feature and wherein the stop feature is configured to inhibit the container from exiting the lumen.

24. The system of claim 23, wherein the filter is the stop feature.

25. A system for delivering a therapeutic agent contained in a container to a patient, comprising:
a flexible catheter configured to follow a non-linear path through the patient, the catheter having a proximal end and a distal end and comprising a body defining a lumen extending from the proximal end to the distal end of the catheter;
a first bar slidably disposable in the lumen, wherein the first bar is configured to force the therapeutic agent out of the container and out of the lumen of the catheter when the container is in proximity to the distal end of the catheter; and
a filter disposed across the catheter lumen in proximity to the distal end of the catheter body, the filter being configured to allow the therapeutic agent to exit the lumen and to prevent unintended particulate matter from exiting the lumen.

26. The system of claim 25, further comprising a stop feature in proximity to the distal end of the catheter, wherein distal movement of the first bar forces the therapeutic agent out of the container and out of the lumen, and wherein the stop feature is configured to inhibit the container from exiting the lumen.

27. The system of claim 25, wherein the filter is the stop feature.

* * * * *